(12) United States Patent
Mu

(10) Patent No.: US 11,135,256 B2
(45) Date of Patent: Oct. 5, 2021

(54) PHARMACEUTICAL COMPOSITION AND USE THEREOF FOR ISCHEMIA TREATMENT

(71) Applicant: Shin-Kong Wu Ho-Su Memorial Hospital, Taipei (TW)

(72) Inventor: Shu-Chi Mu, Taipei (TW)

(73) Assignee: SHIN-KONG WU HO-SU MEMORIAL HOSPITAL, Taipei (TW)

( * ) Notice: Subject to any disclaimer, the term of this patent is extended or adjusted under 35 U.S.C. 154(b) by 5 days.

(21) Appl. No.: 16/699,308

(22) Filed: Nov. 29, 2019

(65) Prior Publication Data

US 2021/0161982 A1   Jun. 3, 2021

(51) Int. Cl.
*A61K 36/00* (2006.01)
*A61K 36/16* (2006.01)
*A61P 9/10* (2006.01)
*A61K 31/365* (2006.01)
*A61K 31/7048* (2006.01)

(52) U.S. Cl.
CPC ............ *A61K 36/16* (2013.01); *A61K 31/365* (2013.01); *A61K 31/7048* (2013.01); *A61P 9/10* (2018.01)

(58) Field of Classification Search
CPC ....................................................... A61K 36/00
USPC .......................................................... 424/725
See application file for complete search history.

(56) References Cited

FOREIGN PATENT DOCUMENTS

CN   105726586 A   7/2016

*Primary Examiner* — Michael V Meller
(74) *Attorney, Agent, or Firm* — Muncy, Geissler, Olds & Lowe, P.C.

(57) ABSTRACT

A pharmaceutical composition for ischemia treatment of a patient includes a ginkgo extraction and a pharmaceutically acceptable carrier. The dosage form of the pharmaceutical composition is gel, transdermal patch, cream or paste. The patient is a neonate, an infant, or an early child. A use of the pharmaceutical composition for ischemia treatment of a patient is disclosed.

10 Claims, No Drawings

PHARMACEUTICAL COMPOSITION AND USE THEREOF FOR ISCHEMIA TREATMENT

BACKGROUND OF THE INVENTION

Field of Invention

The disclosure relates to a pharmaceutical composition for ischemia treatment and a use of the pharmaceutical composition.

Related Art

Ischemia refers to a reduction of blood content in an organ or a tissue, which may be a local performance of systemic anemia or a result of local blood circulation disorders. Ischemia can be divided into limb ischemia or organ ischemia, such as cerebral ischemia (ischemic stroke), cardiac ischemia (ischemic heart disease) and the like according to the location of ischemia. In recent years, due to the population aging, the smoking, the changes in eating habits, and an increase in the proportion of people with diabetes, the incidences of the peripheral arterial occlusive disease have been increased, which leads to an increase in the incidence of limb ischemia. The prevalence may even be as high as 11%. In addition to the peripheral arterial occlusive disease, Raynaud's phenomenon, Buerger's disease, angiospasmodic disease, compression, and the like, may also cause limb ischemia.

Limb ischemia can also occur in neonate, especially premature infant. Its cause is different from that of adults, which may be caused by vascular hypoplasia, hypoxia, anemia, and the like. However, no matter in adults or neonate, limb ischemia may cause numbness, pain or coldness at the end of the limb. As the time of ischemia increases, it is more likely to cause purple, black, and even tissue ulceration and necrosis of the limb.

Traditionally, ischemia has been treated mainly by drugs which are administered orally. However, the drugs administered orally not only act on the location of ischemia but also on the whole body. Therefore, systemic side effects may occur. Moreover, the organs (such as liver, kidney, and the like) of drug metabolism may also influence the action speed and efficacy of the drugs.

Accordingly, it is an urgent need to provide a pharmaceutical composition for ischemia treatment and the use of the pharmaceutical composition. The pharmaceutical composition can directly act on ischemic local tissue to promote blood circulation of the local tissue, which may prevent the local tissue from getting numbness, pain, even purple, black, ulceration or necrosis caused by ischemia. Thus, the efficacy of ischemia treatment can be achieved, and the side effects at other tissue caused by the drugs can be avoided, simultaneously.

SUMMARY OF THE INVENTION

In view of the foregoing objectives, the purpose of the disclosure is to provide a pharmaceutical composition for ischemia treatment and the use of the pharmaceutical composition. The pharmaceutical composition can directly act on ischemic local tissue to promote blood circulation of the local tissue, which may prevent the local tissue from getting numbness, pain, even purple, black, ulceration or necrosis caused by ischemia. Thus, the efficacy of ischemia treatment can be achieved, and the side effects at other tissue caused by drugs can be avoided, simultaneously.

To achieve the above objective, the disclosure provides a pharmaceutical composition for ischemia treatment of a patient. The pharmaceutical composition includes ginkgo extraction and a pharmaceutically acceptable carrier, wherein the dosage form of the pharmaceutical composition is gel, transdermal patch, cream or paste. The patient is a neonate, an infant, or an early child.

To achieve the above objective, the disclosure provides a use of a pharmaceutical composition for ischemia treatment of a patient. The pharmaceutical composition includes a ginkgo extraction and a pharmaceutically acceptable carrier, wherein the dosage form of the pharmaceutical composition is gel, transdermal patch, cream or paste. The patient is a neonate, an infant, or an early child.

In one embodiment, the ginkgo extraction is extracted from ginkgo leaves. The ginkgo extraction includes flavonglycoside and ginkgolide. An amount of the flavonglycoside is 20% or more of the ginkgo extraction. An amount of the ginkgolide is 5% or more of the ginkgo extraction.

In one embodiment, a dose of the ginkgo extraction is between 0.01 mg/ml and 5 mg/ml.

In one embodiment, a dose of the ginkgo extraction is between 0.01 $mg/cm^2$ and 5 $mg/cm^2$.

In one embodiment, the pharmaceutically acceptable carrier is mineral oil, propylene glycol, polyoxypropylene, emulsion wax, glycerol, polyethylene glycol, fatty alcohol, fatty ether, fatty acid ester, vegetable oil, silicone oil, vaseline, lanolin, beeswax, hyaluronic acid, polyacrylic acid, polyvinylpyrrolidone, gelatin, dextrin, polysaccharide, polyacrylamide, polyvinyl alcohol, polyvinyl acetate, hydroxypropyl methylcellulose, or carboxypropyl methylcellulose.

As mentioned above, the efficacy of this disclosure is to provide a pharmaceutical composition for ischemia treatment and the use of the pharmaceutical composition. The pharmaceutical composition can directly act on ischemic local tissue to promote blood circulation of the local tissue, which may prevent the local tissue from getting numbness, pain, even purple, black, ulceration or necrosis caused by ischemia. Thus, the efficacy of ischemia treatment can be achieved, and the side effects at other tissue caused by drugs can be avoided, simultaneously.

DETAILED DESCRIPTION OF THE INVENTION

The embodiments and the examples of the pharmaceutical composition for ischemia treatment and the use for manufacturing thereof of the disclosure will be apparent from the following detailed description, which proceeds with reference to the accompanying tables, wherein the same references relate to the same elements.

The pharmaceutical composition for ischemia treatment and the use of the pharmaceutical composition of the disclosure can directly act on ischemic local tissue to promote blood circulation of the local tissue, which may prevent the local tissue from getting numbness, pain, even purple, black, ulceration or necrosis caused by ischemia. Thus, the efficacy of ischemia treatment can be achieved, and the side effects at other tissue caused by drugs can be avoided, simultaneously.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The term "ischemia" is meant to refer to a reduction of blood content in an organ or a tissue, which may be a local performance of systemic anemia or a result of local blood circulation disorders. Ischemia can be divided into limb ischemia or organ ischemia, such as cerebral ischemia (ischemic stroke), cardiac ischemia (ischemic heart disease) and the like according to the location of ischemia. Limb ischemia may be caused by Raynaud's phenomenon, Buerger's disease, angiospasmodic disease, compression, vascular hypoplasia, hypoxia, anemia, and the like. Limb ischemia may cause numbness, pain or coldness at the end of the limb. As the time of ischemia increases, it is more likely to cause purple, black, and even tissue ulceration and necrosis of the limb.

The term "ginkgo extraction" refers to an extraction which is extracted from the ginkgo leaves. The active ingredients of the ginkgo extraction are flavonglycosides, ginkgolides and the like.

The term "extract" refers to a method for isolating a specific component from a mixture by the different solubility of the different components in the solvent. There are two ways of the extraction which are liquid-liquid extraction and solid-liquid extraction, respectively. Liquid-liquid extraction is a method for isolating a specific component from a liquid mixture. Solid-liquid extraction is a method for isolating a specific component from a solid mixture.

The term "flavonglycosides" is also called "flavonoids" which is meant to refer to a component of the ginkgo leaves extraction. Recently studies indicated that the flavonglycosides have the functions of antioxidation and free-radical removement.

The term "ginkgolides" refers to a component of the ginkgo leaves extraction. Recently studies indicated that the ginkgolides is an antagonist of the platelet-activating factor (PAF) which could promote the activation and aggregation of platelet. In addition, the ginkgolide is also used for treating cerebral vascular disease and migraine.

As used herein, a "disease" is a state of health of a subject wherein the subject cannot maintain homeostasis, and wherein if the disease is not ameliorated then the subject's health continues to deteriorate.

The terms "treat", "treating" and "treatment" as used herein, means reducing the frequency or severity with which symptoms of a disease or condition are experienced by a subject by virtue of administering an agent or pharmaceutical composition to the subject.

As used herein, the term "pharmaceutically acceptable" refers to a material, such as a carrier or diluent, which does not abrogate the biological activity or properties of the ginkgo extraction, or any salt, solvate, hydrate, prodrug, enantiomer, diastereoisomer, or tautomer thereof useful within the disclosure, and is relatively non-toxic, i.e., the ginkgo extraction may be administered to a subject without causing undesirable biological effects or interacting in a deleterious manner with any of the components of the composition in which it is contained.

As used herein, the term "pharmaceutically acceptable carrier" means a pharmaceutically acceptable salts, material, composition or carrier, such as a filler, diluent, excipient, or encapsulating material, involved in applying the ginkgo extraction useful within the invention to the skin surface of the subject such that it may perform its intended function. Each salt or carrier must be compatible with the other ingredients of the formulation, including the ginkgo extraction useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; diluent; granulating agents; lubricating agent; binding agents; disintegrating agents; wetting agents; emulsifying agents; coloring substances; releasing agents; coating agents; aromatic agents; preservatives; antioxidants; plasticizers; gelling agents; thickening agents; hardening agents; setting agents; surface active agents; humectant; carriers; stabilizers; and other non-toxic compatible substances employed in pharmaceutical formulations.

Pharmaceutical compositions that are useful in the methods of the invention may be suitably developed for topical or transdermal routes of administration. Suitable compositions and dosage forms include, for example, but not limited to gel, transdermal patch, cream or paste.

Formulations suitable for topical administration include, but are not limited to, liquid or semi liquid preparations such as liniments, lotions, oil-in-water or water-in-oil emulsions such as creams, ointments or pastes. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

The carriers of the pharmaceutical composition with gel, transdermal patch, cream or pastes dosage form for topical or transdermal routes of administration can include, but not limited to mineral oil, propylene glycol, polyoxypropylene, emulsion wax, glycerol, polyethylene glycol, fatty alcohol, fatty ether, fatty acid ester, vegetable oil, silicone oil, vaseline, lanolin, beeswax, hyaluronic acid, polyacrylic acid, polyvinylpyrrolidone, gelatin, dextrin, polysaccharide, polyacrylamide, polyvinyl alcohol, polyvinyl acetate, hydroxypropyl methylcellulose, or carboxypropyl methylcellulose.

The topically pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another embodiment, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, the terms "patient", "individual" and "subject" can be used interchangeably and may refer to a human or non-human mammal. Non-human mammals include, for example, livestock and pets, such as ovine, bovine, porcine, canine, feline and murine mammals. Preferably, the subject is human.

The term "neonate" refers to a human within 28 days after birth. The term "infant" refers to a human being between 28 days after birth and 1 year old. The term "early child" refers to a human being between 1 and 3 years old. The term "premature infant" refers especially to neonates born between 20 to 37 weeks of pregnancy.

As used herein, the terms "dose" refers to the concentration of the ginkgo extraction which can promote blood circulation. The dose of the ginkgo extraction is between 0.01 mg/ml and 5 mg/ml in the gel, cream or paste of the invention. Preferably, the dose of the ginkgo extraction is between 0.05 mg/ml and 3 mg/ml in the gel, cream or paste of the invention. Preferably, the dose of the ginkgo extraction is between 0.08 mg/ml and 2 mg/ml in the gel, cream or paste of the invention. The dose of the ginkgo extraction is between 0.01 mg/cm$^2$ and 5 mg/cm$^2$ in the transdermal patch of the invention. Preferably, the dose of the ginkgo extraction is between 0.05 mg/cm$^2$ and 3 mg/cm$^2$ in the transdermal patch of the invention. Preferably, the dose of the ginkgo extraction is between 0.08 mg/cm$^2$ and 2 mg/cm$^2$ in the transdermal patch of the invention.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

A pharmaceutical composition of the disclosure is used for ischemia treatment of a patient. The pharmaceutical composition includes a ginkgo extraction and a pharmaceutically acceptable carrier, wherein the dosage form of the pharmaceutical composition is gel, transdermal patch, cream or paste. In this embodiment, a dose of the ginkgo extraction can be taken or weighted, and then added to a pharmaceutically acceptable carrier to prepare a pharmaceutical composition. The pharmaceutical composition is administered to the ischemic location of the patient to achieve the efficacy of promoting blood circulation at the location.

In addition, the dosage form of the pharmaceutical composition of this invention includes gel, transdermal patch, cream or paste. In this embodiment, when the dosage form of the pharmaceutical composition is gel, cream or paste, the dose of the ginkgo extraction is between 0.01 mg/ml and 5 mg/ml. Preferably, the dose of the ginkgo extraction is between 0.05 mg/ml and 3 mg/ml. Preferably, the dose of the ginkgo extraction is between 0.08 mg/ml and 2 mg/ml. In this embodiment, when the dosage form of the pharmaceutical composition is transdermal patch, the dose of the ginkgo extraction is between 0.01 mg/cm$^2$ and 5 mg/cm$^2$. Preferably, the dose of the ginkgo extraction is between 0.05 mg/cm$^2$ and 3 mg/cm$^2$. Preferably, the dose of the ginkgo extraction is between 0.08 mg/cm$^2$ and 2 mg/cm$^2$. Of course, the dose of the ginkgo extraction may be any value and range encompassed between any two values within the foregoing ranges and may be changed according to the carrier which is used, the route of administration, or the individual who in need and the physiology state thereof.

In this embodiment, the ginkgo extraction is extracted from ginkgo leaves. The ginkgo extraction includes a flavonglycoside and a ginkgolide. More than 20% of the ginkgo extraction is the flavonglycoside and more than 5% of the ginkgo extraction is the ginkgolide. Preferably, more than 24% of the ginkgo extraction is the flavonglycoside and more than 6% of the ginkgo extraction is the ginkgolide.

In this embodiment, the pharmaceutically acceptable carrier is mineral oil, propylene glycol, polyoxypropylene, emulsion wax, glycerol, polyethylene glycol, fatty alcohol, fatty ether, fatty acid ester, vegetable oil, silicone oil, vaseline, lanolin, beeswax, hyaluronic acid, polyacrylic acid, polyvinylpyrrolidone, gelatin, dextrin, polysaccharide, polyacrylamide, polyvinyl alcohol, polyvinyl acetate, hydroxypropyl methylcellulose, or carboxypropyl methylcellulose. Preferably, the pharmaceutically acceptable carrier is vaseline.

In this embodiment, "ischemia" refers to "limb ischemia", which also called "limb ischaemia". Limb ischemia includes but not limited to "chronic limb ischemia" or "acute limb ischemia".

In this embodiment, the patient is a neonate, an infant, or an early child. Preferably, the patient is a premature infant of the neonate.

This invention also provides a use of a pharmaceutical composition for ischemia treatment of a patient. In addition, this invention further provides a method for treating ischemia. The method includes a step of applying a pharmaceutical composition to the affected area of a patient who suffers by ischemia. The pharmaceutical composition includes a ginkgo extraction and a pharmaceutically acceptable carrier. The dosage form of the pharmaceutical composition is gel, transdermal patch, cream or paste. The ischemia refers to "limb ischemia". The patient is a premature infant. The concentration or dose of the pharmaceutical composition, the types of the carriers, and other properties are mostly the same as those of the pharmaceutical composition described above, and therefore is omitted here for conciseness.

As mentioned above, the pharmaceutical composition and the use of the pharmaceutical composition of the invention can directly act on ischemic local tissue to promote blood circulation of the local tissue, which may prevent the local tissue from getting numbness, pain, even purple, black, ulceration or necrosis caused by ischemia. Thus, the efficacy of ischemia treatment can be achieved, and the side effects at other tissue caused by drugs can be avoided, simultaneously.

To illustrate the efficacy of the use and the pharmaceutical composition of this invention for limb ischemia improvement, there are several examples shown below.

EXAMPLE 1

Preparation of the Pharmaceutical Composition 0.08 mg to 2 mg of the ginkgo extraction (trade name GINCARE FC TAB 40 MG, YUNGSHIN PHARM IND. CO. LTD.) and 1 ml of sterile gel (CEYOTEK Patient Lubricant (Sterile), Ceyotek Technology Co., Ltd.) were mixed to make a pharmaceutical composition. The dose (concentration) of the ginkgo extraction of the pharmaceutical composition is between 0.08 mg/ml and 2 mg/ml and used in the subsequent experimental example 2.

EXAMPLE 2

The Study Result of the Ginkgo Extraction for Improving the Limb Ischemia of Premature Infants Patients in this Study:

Premature infants with limb ischemia were treated at Shin Kong Wu Ho-Su Memorial Hospital in Taiwan from June 2018 to December 2019. The informed consent to participate which are approved by the Institutional Review Board of the hospital are signed by the parents or guardians of the premature infants.

TABLE 1

Patient status and treatment information

| Patient status and treatment information | Patient 1 | Patient 2 | Patient 3 |
|---|---|---|---|
| Gestational age | 29 weeks | 26 weeks | 26 weeks + 4 days |
| Birthweight (g) | 865 | 990 | 930 |
| Gender | male | female | male |
| Age when the ischemia occurred (days) | 2 | 2 | 1 |
| Bodyweight when the ischemia occurred(g) | 830 | 950 | 930 |
| The usage dose (mg/ml) | 0.08 | 0.08 | 0.5-2 |
| Time to improvement | 3 hours | 3.2 hours | 10 days |
| Duration of treatment | 4 hours | 4 hours | 24 days |
| Arterial/venous catheterization | Venous catheter | Venous catheter | Arterial catheter |

Treatment Method which Using the Pharmaceutical Composition of the Present Invention.

The pharmaceutical composition prepared in Example 1 was applied to the ischemic location (affected area) of Patient 1, Patient 2 and Patient 3. The application thickness is about 1 mm, and the application area changes depending on the area of the affected area. The affected area needs to be completely covered. After application, a layer of gauze was covered to the affected area. The affected area was then warmed for 30 minutes to allow the pharmaceutical composition to be absorbed. The gauze was then removed from the affected area to apply a new layer of the pharmaceutical composition. A new layer of gauze was covered to the affected area and allowed to stand for 30 minutes (not to be warmed). All of the foregoing steps were combined to be a single course of the treatment. Repeat the above treatment which has following steps at the affected area until the affected area has improvement: applying the pharmaceutical composition, covering with a layer of gauze and warming for 30 minutes, removing the gauze, applying the pharmaceutical composition, covering with a new layer of gauze and standing for 30 minutes (not to be warmed). When the ischemic condition has significant improvement, the condition was recorded, and then the treatment was continued until the affected area was completely resolved.

Please refer to Table 1 to illustrate the treatment condition of Patient 1. As shown in Table 1, the ischemia symptom of Patient 1 occurred at 2 days after birth. The ischemia symptom of Patient 1 was observed to be improved after 3 hours of treatment (i.e. 3 courses of treatment were applied). In addition, the ischemia symptom of Patient 1 was completely resolved after 4 hours of treatment (i.e. 4 courses of treatment were applied).

Please refer to Table 1 to illustrate the treatment condition of Patient 2. As shown in Table 1, the ischemia symptom of Patient 2 occurred at 2 days after birth. The ischemia symptom of Patient 2 was observed to be improved after 3.2 hours of treatment (i.e. 3 courses of treatment were applied). In addition, the ischemia symptom of Patient 2 was completely resolved after 4 hours of treatment (i.e. 4 courses of treatment were applied).

Please refer to Table 1 to illustrate the treatment condition of Patient 3. As shown in Table 1, the ischemia symptom of Patient 3 occurred at 1 day after birth. The ischemia symptom of Patient 3 was observed to be improved after 10 days of treatment. In addition, the ischemia symptom of Patient 3 was completely resolved after 24 days of treatment.

The pharmaceutical composition of the embodiment of the present invention can improve and even resolve the condition of the limb (toe) ischemia in premature infants according to the results of the above examples. In particular, the treatment of limb ischemia in premature infants is merely one of the examples for illustrating the pharmaceutical composition of the present application. The pharmaceutical composition of the present invention and the use of the pharmaceutical composition can also be applied for neonates who is not premature infants, infants or even early children, and is not intended to be limiting. The treated location can also be used for other parts such as, but not limited to, a finger, an arm, a calf, a thigh, and the like. Further, although the carrier used in the pharmaceutical composition of the above example is a gel for illustration, the pharmaceutical composition may include other carriers described herein and is not intended to be limiting.

As mentioned above, the pharmaceutical composition for ischemia treatment and the use of the pharmaceutical composition of the disclosure can directly act on ischemic local tissue to promote blood circulation of the local tissue, which may prevent the local tissue from getting numbness, pain, even purple, black, ulceration or necrosis caused by ischemia. Thus, the efficacy of ischemia treatment can be achieved, and the side effects at other tissue caused by drugs can be avoided, simultaneously.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method for treating ischemia in a patient in need thereof, comprising administering a pharmaceutical composition to an ischemic location of the patient, covering the ischemic location by a gauze, warming the ischemic location for 30 minutes, removing the gauze, administering the pharmaceutical composition to the ischemic location, and covering the ischemic location for 30 minutes by a new gauze, wherein the pharmaceutical composition comprises a ginkgo extraction and a pharmaceutically acceptable carrier, the dosage form of the pharmaceutical composition is gel, cream or paste, and the patient is a premature infant, wherein a dose of the ginkgo extraction is between 0.01 mg/ml and 5 mg/ml.

2. The method of claim 1, wherein the ginkgo extraction is extracted from ginkgo leaves, the ginkgo extraction comprises flavonglycoside and ginkgolide, an amount of the flavonglycoside is 20% or more of the ginkgo extraction, and an amount of the ginkgolide is 5% or more of the ginkgo extraction.

3. The method of claim 1, wherein the pharmaceutically acceptable carrier is mineral oil, propylene glycol, polyoxypropylene, emulsion wax, glycerol, polyethylene glycol, fatty alcohol, fatty ether, fatty acid ester, vegetable oil, silicone oil, vaseline, lanolin, beeswax, hyaluronic acid, polyacrylic acid, polyvinylpyrrolidone, gelatin, dextrin, polysaccharide, polyacrylamide, polyvinyl alcohol, polyvinyl acetate, hydroxypropyl methylcellulose, or carboxypropyl methylcellulose.

4. The method of claim 1, wherein the pharmaceutical composition is administered to the ischemic location of the patient with about 1 mm thickness.

5. The method of claim 1, wherein the ischemic location has no wound.

6. A method for treating ischemia in a patient in need thereof, comprising administering a pharmaceutical composition to an ischemic location of the patient, covering the ischemic location by a gauze, warming the ischemic location for 30 minutes, removing the gauze, administering the pharmaceutical composition to the ischemic location, and covering the ischemic location for 30 minutes by a new gauze, wherein the pharmaceutical composition comprises a ginkgo extraction and a pharmaceutically acceptable carrier, the dosage form of the pharmaceutical composition is transdermal patch, and the patient is a premature infant, wherein a dose of the ginkgo extraction is between 0.01 mg/cm$^2$ and 5 mg/cm$^2$.

7. The method of claim 6, wherein the ginkgo extraction is extracted from ginkgo leaves, the ginkgo extraction comprises flavonglycoside and ginkgolide, an amount of the flavonglycoside is 20% or more of the ginkgo extraction, and an amount of the ginkgolide is 5% or more of the ginkgo extraction.

8. The method of claim 6, wherein the pharmaceutically acceptable carrier is mineral oil, propylene glycol, polyoxypropylene, emulsion wax, glycerol, polyethylene glycol, fatty alcohol, fatty ether, fatty acid ester, vegetable oil, silicone oil, vaseline, lanolin, beeswax, hyaluronic acid, polyacrylic acid, polyvinylpyrrolidone, gelatin, dextrin, polysaccharide, polyacrylamide, polyvinyl alcohol, polyvinyl acetate, hydroxypropyl methylcellulose, or carboxypropyl methylcellulose.

9. The method of claim 6, wherein the pharmaceutical composition is administered to the ischemic location of the patient with about 1 mm thickness.

10. The method of claim 6, wherein the ischemic location has no wound.

* * * * *